(12) United States Patent
Mrsny et al.

(10) Patent No.: US 9,733,254 B2
(45) Date of Patent: Aug. 15, 2017

(54) METHODS AND APPARATUS FOR THE IN VITRO MODELLING OF DRUG ADMINISTRATION

(71) Applicant: THE UNIVERSITY OF BATH, Bath and North East Somerset (GB)

(72) Inventors: Randall Jay Mrsny, Bath and North East Somerset (GB); Hanne Maarit Kinnunen, Bath and North East Somerset (GB)

(73) Assignee: The University of Bath, Bath (GB)

( * ) Notice: Subject to any disclaimer, the term of this patent is extended or adjusted under 35 U.S.C. 154(b) by 0 days.

(21) Appl. No.: 14/433,760

(22) PCT Filed: Oct. 3, 2013

(86) PCT No.: PCT/GB2013/052578
§ 371 (c)(1),
(2) Date: Apr. 6, 2015

(87) PCT Pub. No.: WO2014/053840
PCT Pub. Date: Apr. 10, 2014

(65) Prior Publication Data
US 2015/0247864 A1    Sep. 3, 2015

(30) Foreign Application Priority Data

Oct. 4, 2012  (GB) .................................. 1217768.9

(51) Int. Cl.
*G01N 13/00*    (2006.01)
*G01N 33/15*    (2006.01)
(Continued)

(52) U.S. Cl.
CPC ......... *G01N 33/6842* (2013.01); *G01N 13/00* (2013.01); *G01N 33/50* (2013.01);
(Continued)

(58) Field of Classification Search
CPC ............. G01N 13/00; G01N 2013/003; G01N 2013/006; G01N 33/15
See application file for complete search history.

(56) References Cited

U.S. PATENT DOCUMENTS

| 4,812,407 A | 3/1989 | Buchmann et al. |
| 5,244,799 A * | 9/1993 | Anderson ................. A61F 2/14 424/487 |

(Continued)

FOREIGN PATENT DOCUMENTS

| EP | 2182342 | 5/2010 |
| WO | 00/46597 | 8/2000 |

OTHER PUBLICATIONS

Son Y J et al: "Development of a standardized dissolution test method for inhaled pharmaceutical formulations", International Journal of Pharmaceutics, Elsevier BV, NL, vol. 382, No. 1-2, Dec. 1, 2009 (Dec. 1, 2009), pp. 15-22.
(Continued)

*Primary Examiner* — Paul Hyun
(74) *Attorney, Agent, or Firm* — Stites & Harbison PLLC; Richard S. Myers, Jr.

(57) ABSTRACT

Methods and apparatus for the in vitro modelling of changes that occur on administration of a drug formulation are described, in particular for studying the changes that take place on administration of protein or peptide drug formulations by subcutaneous injection.

27 Claims, 4 Drawing Sheets

(51) Int. Cl.
G01N 33/68 (2006.01)
G01N 33/50 (2006.01)
G01N 21/64 (2006.01)
G01N 21/65 (2006.01)

(52) U.S. Cl.
CPC .............. G01N 21/64 (2013.01); G01N 21/65 (2013.01); G01N 33/15 (2013.01); G01N 2013/003 (2013.01); G01N 2013/006 (2013.01); G01N 2570/00 (2013.01)

(56) References Cited

U.S. PATENT DOCUMENTS

2005/0106545 A1* 5/2005 Heruth .................... G09B 23/34
434/267
2006/0034807 A1* 2/2006 Griffith .................... A61L 27/26
424/93.7
2011/0053207 A1* 3/2011 Hoganson ............... A61L 27/18
435/29

OTHER PUBLICATIONS

Susan S D'Souza et al: "Methods to Assess in Vitro Drug Release from Injectable Polymeric Particulate Systems", Pharmaceutical Research, Kluwer Academic Publishersplenum Publishers, NL, vol. 23, No. 3, Mar. 1, 2006 (Mar. 1, 2006), pp. 460-474.
Andrews Gavin P et al: "Characterisation of the Thermal, Spectroscopic and Drug Dissolution Properties of Mefenamic Acid and Polyoxyethylene-Polyoxypropylene Solid Dispersions", Journal of Pharmaceutical Sciences, vol. 98, No. 12, Dec. 2009 (Dec. 2009), pp. 4545-4556.
David C. Browne, Shawn Kieselmann: "Low-Level Drug Release-Rate Testing of Ocular Implants Using USP Apparatus 4 Dissolution and HPLC End Analysis", Dissolution Technologies, vol. 17, No. 1, Feb. 1, 2010 (Feb. 1, 2010), pp. 12-14.

* cited by examiner

METHODS AND APPARATUS FOR THE IN VITRO MODELLING OF DRUG ADMINISTRATION

CROSS REFERENCE TO RELATED APPLICATIONS

This application is a §371 National State Application of PCT/GB2013/052578 filed Oct. 3, 2013 which claims priority to GB 1217768.9 filed Oct. 4, 2012.

FIELD OF THE INVENTION

The present invention relates to methods and apparatus for the in vitro modelling of changes that occur on administration of a drug formulation, and in particular on administration of protein or peptide drug formulations by subcutaneous injection.

BACKGROUND OF THE INVENTION

Chronic therapies involving protein or peptide drugs to treat conditions such as diabetes, cancer, hepatitis, and osteoporosis represent the continuing shift of the pharmaceutical industry toward biotherapeutics. Due to lifestyle issues and an aging population, the number of patients requiring these medications is growing rapidly. Health care economics often require these agents to be administered without office visits, mandating the need for formulations that allow for subcutaneous (SC) injection, rather than intravenous (IV) infusion. No predictive model for SC injection outcomes in man has been identified; the prospect of clinically testing a number of formulations is prohibitively expensive. Thus, development programs for many promising agents are often halted when formulations identified with sufficient shelf-life stability and sufficient preclinical efficacy result in low or variable bioavailability (% BA) following SC injection when tested in the clinic. Such outcomes result in significant lost opportunity costs, imparting a substantial addition to research and development costs that are ultimately reflected in drug pricing, which impacts overall healthcare expenses.

There are several reasons for this state of the affairs. The first is that there is limited knowledge of what a protein or peptide in a formulation experiences during the critical first hour following administration, in particular by subcutaneous injection, and without this information, formulation scientists cannot design formulations to take account of these processes. Thus, rather than addressing the problem of understanding what happens when a biotherapeutic is administered, formulation scientists and regulatory authorities can only focus on extending the shelf life of the formulation prior to administration by attempting to minimise conflicting chemical and physical degradation pathways and to hope that this is compatible for (e.g.) subcutaneous injection. Current subcutaneously administered formulations typically have a 2 to 3 year shelf life using pH 5-6 and various combinations excipients such as detergents, preservatives, sugars and/or human albumin. However, with no information regarding the events that take place on administration and at the injection site, there is no systematic approach to address problem of poor or variable bioavailability through formulation changes. The present invention attempts to address this unmet need in the art.

U.S. Pat. No. 4,812,407 describes an apparatus for testing the diffusion behaviour of a drug in which a radiolabelled drug is introduced into a donor compartment and allowed to diffuse through a membrane into a surrounding acceptor compartment. A measuring device such as a scintillation counter is used to detect the quantity or concentration of the radiolabelled drug in the acceptor compartment.

EP 2182342 discloses an apparatus and method for testing dissolution of a drug using a chamber with two compartments separated by a membrane which is permeable to dissolved drug, but impermeable to the drug in an undissolved form. A similar approach is disclosed in WO 00/46597.

SUMMARY OF THE INVENTION

Broadly, the present invention aims to provide apparatus and methods that are capable of determining changes in the properties of a drug formulation that occur on administration, especially administration by injection (e.g. subcutaneous injection), and how these changes affect physicochemical properties of the drugs present in the formulations, such as the stability of the formulation or the bioavailability of the drug. The apparatus and methods are particularly useful for testing formulations of biological therapeutics such as proteins, antibodies and peptides. This in vitro model is designed to model simultaneously the multiple stressors that drug formulation, such as a protein, peptide or antibody formulation, experience once it has been injected into an administration site in a body, such as subcutaneous space, by using a membrane cassette designed to simulate the conditions and components present at the administration, and allow components of the formulation to be tested in the membrane cassette, as well as in the surrounding sink into which components of the formulation can diffuse. Such a model can be used to assess specific formulation components as a way to optimise drug formulations by changing parameters, conditions and/or properties of the formulation and testing to see whether the changes improve the outcome on administration. It also may be used to provide data for regulatory filings or for quality control purposes.

Unlike the apparatus and methods disclosed in U.S. Pat. No. 4,812,407, the present invention allows changes in a property of the drug or drug formulation to be determined inside the membrane cassette, as well as optionally also in the surrounding bath, and enables measurements to be made on one or more properties of drug formulation that go beyond the simple determination of its diffusion or dissolution behaviour through a porous membrane in a two chamber system.

Accordingly, in a first aspect, the present invention provides an in vitro method of determining a change in a property of a drug formulation that occurs on administration, the method employing an apparatus that comprises:
  a membrane cassette comprising a chamber having a membrane, the membrane having perforations through which components of the drug formulation are capable of diffusing for simulating changes that occur on administration of the drug formulation;
  a bath for containing the membrane cassette and a surrounding liquid medium;
  a probe capable of detecting a change in a property of the drug formulation in the membrane cassette, and optionally a change in a property of the drug formulation in the bath,
  wherein the method comprises the steps of:
    (a) arranging the membrane cassette in the bath;
    (b) introducing the drug formulation into the chamber of the membrane cassette;

(c) optionally changing one or more components or conditions of the drug formulation or the liquid medium; and (d) determining the change of the property of the drug formulation using the probe.

In a further aspect, the present invention provides an apparatus for determining a change in a property of a drug formulation that occurs on administration, the apparatus comprising:

a membrane cassette comprising a chamber having a membrane, the membrane having perforations through which components of the drug formulation are capable of diffusing for simulating changes that occur on administration of the drug formulation;

a bath for containing the membrane cassette and a surrounding liquid medium;

a probe capable of detecting a change in a property of the drug formulation in the membrane cassette, and optionally a change in a property of the drug formulation in the bath, wherein in use the membrane cassette is arranged in the bath and the drug formulation is introduced into the chamber of the membrane cassette thereby enabling changes in the property of the drug formulation to be determined using the probe.

The present invention therefore provides methods and apparatus for modelling the changes that occur in a drug formulation on administration. In one preferred embodiment, this can be used to model subcutaneous administration (e.g. subcutaneous injection), for which there is currently no effective way of studying in the prior art. Thus, in the present invention, the membrane cassette provides a defined site that can be used to model the administration of a drug formulation introduced into a body cavity, organ or via a given route of administration, thereby enabling the effect of modifying the drug formulation or the manner in which it is administered to be studied. For example, by including one or more components present at the site of administration of the drug formulation, for example by having a component of the extracellular matrix contained inside the membrane cassette, the interactions between the extracellular matrix and the formulation components to take place and be amenable to study. Any formulation components that are not bound to the extracellular matrix in the cassette upon injection can then diffuse to the infinite sink provided by the bath surrounding the cassette, from where they can be sampled. Preferably, the liquid medium in the bath surrounding the membrane cassette is a buffer solution. Generally, this will mean that the components of the membrane cassette will be different to the surrounding bath of buffer solution.

More generally, by selecting an appropriate membrane and the contents of the membrane cassette, the behaviour or drug formulations introduced into other body cavities, organs or via other routes of administration may be studied. For example, the vitreous humour of the eye is a hydrogel comprised of collagen and hyaluronic acid, and confined by relatively impermeable sclera and retina. The formulation behaviour of drugs administered in the vitreous compartment of the eye can therefore also be simulated with the apparatus of the present invention by selecting a membrane with permeability properties simulating the eye and filling the membrane cassette with hydrogels similar to the vitreous compartment. Similarly, intramuscular injections can be simulated by using for example actin, myosin, glycogen, myoglobin, collagen, troponin and/or tropomysin in the cassette in conjunction with a membrane with suitable permeability properties. Intradermal injections can be modelled by altering the composition of the extracellular matrix components to collagen and dermatan sulphate; intrathecal injections by using simulated cerebrospinal fluid as the buffer solution and epidural injections by modelling the loose connective tissue composed of collagen and hyaluronic acid filling the epidural space. In this way, the present invention allows the apparatus and methods to be used for modelling the behaviour of drugs on injection, e.g. via subcutaneous, intramuscular, intradermal, intrathecal or epidural routes. The sites in the body that can be modelled therefore include, but are not limited to, the eye, the skin (within and under), muscle, spinal canal or back.

The methods of the present invention may comprise the step of modifying one of the properties of the formulation and repeating one or more of steps (a) to (d) to determine whether there is a change in a property of a drug formulation as compared to other tested drug formulations. Alternatively or additionally, this may include the step of optionally modifying one or more components or conditions present in the chamber of the membrane cassette, for example to determine how selection of the site of administration affects the properties of the drug formulation, such as its bioavailability, and optionally repeating these steps. The effect of modifying a component or condition present inside the chamber of the membrane cassette may be determined in a similar manner to the determination of changes in the drug formulation using the probes that are present with the apparatus.

While the present invention is particularly well suited for studying the changes that occur on administration of biological therapeutics such as protein, peptide or antibody drugs, it may be adapted by the skilled person to studying any type of drug formulation, including small molecule drugs, or nucleotides, gene therapies, or liposomal formulations of drugs.

By way of example, in the present invention, the chamber of the membrane cassette may conveniently have a volume between 0.5 ml and 10 ml. In some cases, the membrane may be transparent, thereby allowing visual inspection of the contents of the chamber as well as access for probes located outside of the cassette via an interrogation path through the membrane. Alternatively, other formats or designs of cassette can be contemplated in which the contents of the cassette may be interrogated using one or more probes having access via walls of the cassette other than the wall(s) in which the membrane is located, for example via two opposing and substantially parallel transparent walls of the cassette. In one particular embodiment, a membrane cassette with a generally square cross-section comprises one pair of opposing walls in which membranes are located, with the other pair of opposing walls being transparent, thereby providing an interrogation path (e.g. a light path) through which probes can make measurements on the contents of the cassette.

The material used for the membrane may be selected by the skilled person from suitable materials well known in the art, and includes membranes formed from materials such as cellulose esters. Other materials that may be used for the membrane include, for example, regenerated cellulose, cellulose acetate or ester or mixture of thereof, polycarbonate, polyester, polyestersulfone, nylon, polyvinylidinefluoride (PVDF), polyvinylchloride (PVC) or polytetrafluoroethylene (PTFE). There are many examples of suitable membranes available from commercial sources such as Whatman, Millipore, Pierce or Biodesign.

In one embodiment, the membrane cassette may have cuvette type design in which the sides of the cuvette provide the interrogation path through which the probe can make measurements on a drug formulation contained inside the cuvette. For example, in a cuvette with a square cross-section, two opposing walls may be transparent to light for providing an interrogation path (i.e. a light path) through the cassette for monitoring the contents of the cassette. The transparent sides for the light path can be obtained by using transparent membrane or by modifying a cuvette, such that a light path remains through the cuvette. This may be achieved several ways. The cuvette may be square or wedge shaped in vertical cross-section provided that the two opposite walls of the cuvette are substantially parallel to each other allowing a light path through the cuvette. The membrane can then be located elsewhere in the cuvette and the membranes do not have to be transparent as the light path for monitoring the contents of the cassette is achieved through the transparent cuvette walls.

If the cuvette-based designs are used, the top of the cuvette may be sealed with a lid system, for example made of Teflon, through which inlets may be placed that can be used for an injection needle port as well as for inserting probes to monitor cassette contents. A stirring mechanism can be inserted within the cassette too, for example a magnetic flea or mechanical stirrer.

As explained herein, an important function of the membrane is to allow diffusion of components of the formulation, and in particular the drug, from the chamber of the membrane cassette into the surrounding bath in a manner which is capable of simulating the changes in the properties and conditions that a drug formulation is exposed to on subcutaneous injection. One feature of the membrane that helps to provide this effect are the apertures in the membrane that provide a path through which the components of the drug formulation are capable of diffusing. Membranes with suitable permeability characteristics such as microfiltration membranes or dialysis membranes can be obtained commercially from sources such as Whatman or Millipore (microfiltration membranes) or Biodesign (dialysis membranes). Alternatively, in order to control the size and spacing of the apertures, the present invention has found that it can be particularly useful to modify commercially available membranes, and in particular that good results may be obtained by treating a membrane with a microneedle roller, such as a DERMAROLLER (http://www.dermaroller.com/). Alternatively, other techniques for producing apertures may be employed, for example using other mechanical means for making apertures or a laser. In general, if perforations are made, it is preferred that the perforations are between about 0.1 and about 200 microns, and optionally between about 0.1 and 10 microns, in size and/or that the perforations are between about 1 micron and 10 mm apart, optionally between about 10 microns and 10 mm apart, and optionally between about 0.1 and 10 mm apart.

However, in some embodiments, for example where the administration of small molecules is being modelled, or where the permeability properties of the injection site are restricted in terms of molecular transport, such as in the vitreous compartment of the eye, it may not be necessary to treat a membrane to make additional perforations, and instead to allow the drug formulation to diffuse through the membrane by virtue of the microscopic perforations present in the material from which the membrane is formed, e.g. a commercially available microfiltration or dialysis membrane.

In addition to the membrane cassette and the surrounding bath, the apparatus of the present invention may include one or more other elements useful for controlling the environment or conditions in the dialysis cassette and/or the bath. By way of example, these optional elements may include heat control and temperature measurement systems for maintaining temperature control and convective flow that simulates diffusional events for a drug within the subcutaneous injection site and uptake of a drug from the subcutaneous injection site through lymphatic system and blood capillaries. Conveniently, this can be achieved by using a heat source such as a hot plate linked to a thermometer or thermocouple capable of being set to a desired temperature, typically in the physiological range. Preferably, a stirrer, e.g. a magnetic or mechanical stirrer, is used for distributing heat in the bath.

Preferably, the membrane cassette further comprises an injection port for introducing samples of drug formulation or probes into the chamber of the cassette. The injection port may be provided as distinct structure of the cassette or the lid system, or injection of sample may be carried out by injecting the sample through a septum, for example a silicone septum sealing a pair of membranes together to create the chamber.

Preferably, the apparatus further comprises means for adjusting the height or volume of the buffer above the membrane cassette for modifying the hydrostatic pressure the membrane cassette is under for simulating conditions at an injection site.

As described herein, the apparatus of the present invention further comprises one or more probes making measurements in the membrane cassette and/or the bath. Preferably, the apparatus comprises a plurality of probes, for example a Raman probe and/or fluorescence spectroscopy probe for monitoring the conformational changes the protein drug undergoes after the injection and for monitoring the protein and excipient concentrations, a temperature probe, a pH probe, a probe for measuring optical density for determining precipitation of components of the formulation, such as a spectrophotometer. Optical density is a particularly useful measure of stability as a loss of stability may cause opalescence and turbidity in drug formulations.

In order to simulate the in vivo environment at a subcutaneous injection site, it is preferred that the membrane cassette contains one or more extracellular matrix components present in subcutaneous tissue. By way of example, the extracellular matrix components may comprise one or more of a hyaluronic acid or a salt thereof, a collagen, a fibronectin, a laminin and/or dermatan sulphate. Alternatively or additionally, one or more cell lines can be added in the cassette. Hyaluronic acid (HA) is a gel like substance present in the subcutaneous tissue filling the void spaces within the extracellular matrix. It has been shown that adding hyaluronidase, an enzyme capable of degrading hyaluronic acid, to subcutaneously injected antibody formulations improves the bioavailability of the antibody. Without wishing to be bound by any particular theory, this may be attributed to the breakage of the gel like diffusion barrier upon the administration of hyaluronidase, resulting in the large antibody molecules diffusing in the subcutaneous space more freely and thus being absorbed through the capillaries and the lymphatic system more readily (see US 2011/0066111). In particular, one of the reasons that hyaluronic acid may be useful in the present invention is that it is negatively charged at physiological pH such that some of the bioavailability issues faced with subcutaneously administered drug formulations may be due to interaction between hyaluronic acid and positively charged molecules present in the formulation. Accordingly, the methods and apparatus of the present invention allow drug formulations, such as therapeutic protein formulations, to be tested to determine the extent to which they interact with hyaluronic acid and other components of the extracellular matrix and hence cause a reduction in the bioavailability of the drug. This enables the present invention to be used to modify the formulations, either by changing the components or conditions present, in order to reduce such unfavourable interactions.

In a further aspect, the present invention provides a method which comprises having optimised a drug formulation according to the methods of the present invention, the further step of manufacturing the drug formulation that comprises one or more changes to an initial formulation.

One use that is envisaged for the apparatus and methods of the present invention is in the testing of drug formulations to obtain data about them to determine consistency of performance following administration, for example by subcutaneous (SC) injection. Such a method may be useful for providing data for quality control, release testing or for fulfilling obligations for regulatory authorities, such as the Food and Drug Administration (FDA) or European Medicines Evaluation Agency (EMEA). As described above, at the present time, there is no satisfactory way of testing the stability and/or the bioavailability of a drug formulation after it has been administered by SC injection. There is also no method to predict the fate of a material prior to its SC injection. This means that the information that regulatory authorities currently require in an application for the approval of a drug relates to the shelf life of the drug formulation prior to administration. This in turn means that the composition of drug formulations is designed with in vitro storage stability in mind, instead of fate or bioavailability of the drug after administration. The present invention has the advantage that by modelling events that could occur immediately upon and for periods of time after administration. It is anticipated that drug properties that affect their fate after (e.g.) SC injection that are identified in this apparatus using the methods described could be useful in the selection of formulation components and their concentrations for the optimization of both shelf life and bioavailability parameters. Accordingly, in further aspect, the present invention provides a data carrier on which data relating to the testing or a drug formulation obtained by the methods of the present invention has been saved, for example for regulatory or for quality control purposes.

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION

General Considerations

Figure 1:
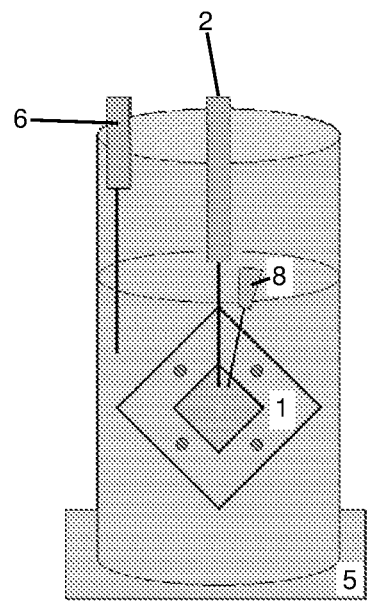
FIG. 1. Schematic representation of a system designed for monitoring the stability of biopharmaceuticals after subcutaneous (sc) injection.

The apparatus and methods of the present invention provide a membrane cassette-based modelling system that is capable of determining changes in the properties of proteins or peptides present in the formulations that occur on administration. In particular, the apparatus and methods disclosed herein enable time course experiments to be carried out that monitor a formulation over a time course, for example over several (e.g. 1 to 6) hours, with parameters that model events anticipated to occur following, for example, an injection such as an injection via a subcutaneous, intramuscular, intradermal, intrathecal or epidural route, and preferably via a subcutaneous (SC) injection, and in particular changes to a drug formulation that take place inside the membrane cassette. Examples of the apparatus of the present invention are described herein which have been constructed using the following elements.

Firstly, it is important for the membrane cassette provide properties and/or conditions that are consistent with diffusion and other events that take place at a site of administration in a human or animal body, such as a subcutaneous injection site. In some aspects, this is achieved using a membrane that has perforations that enable components of the drug formulation to diffuse from the cassette into the bath of buffer solution. By way of example, a commercial dialysis membrane may optionally be modified to produce a membrane with series of very small apertures that provide pathway properties consistent with the subcutaneous injection site, both in terms of the size and spacing of the apertures. In the examples described below of an embodiment of the present invention, two sheets of a modified dialysis membrane are mounted in a membrane cassette on either side of a septum, preferably formed from silicone, to provide a chamber once the two halves of the cassette are locked into place. Advantageously, the septum allows the contents of the membrane cassette to be monitored using one or more probes that may conveniently access the cassette through the membrane, e.g. where it is transparent to radiation, in a needle-type format through the septum, and/or via one or more ports provided in the membrane cassette. Examples of probes useful in experiments carried out using the apparatus of the present invention include pH probes, probes for Raman spectroscopy, temperature probes, pressure transducers, probes for measuring optical density for determining precipitation of components of the formulation, such as a spectrophotometer. In use, the probes may be prepared for experiments by being positioned to take measurement of the contents of the membrane cassette and/or optionally in the surrounding bath. Raman probes are particularly useful for measuring conformational changes that protein drugs go through after the injection and the concentration of the protein and the excipients present in the formulation. These techniques are well adapted to the present invention being capable of determining changes that take place in a drug formulation while it is present inside the membrane cassette, as distinct from simply sampling diffusion of components the formulation into the surrounding sink.

Additionally, the apparatus of the present invention may be provided with a needle system for use in introducing test formulations into the membrane cassette chamber to initiate an experiment. Generally, the membrane cassette will contain one or more components to model the materials and conditions found at a site of administration, for example by filling the membrane cassette with one or more of a hyaluronic acid or a salt thereof, a collagen, a fibronectin, a laminin, dermatan sulphate and/or one or more cell lines. Examples of components useful for simulating conditions at different sites are disclosed elsewhere in the present application. The membrane cassette and/or the bath are then fitted with the probes for use in the experiment, typically at least a pH probe and a Raman probe, and the needle system for introducing test formulations is arranged in place. Warmed physiological media, such as a bicarbonate based buffer, sufficient to establish the desired pressure against the membrane is placed into the infinite sink bath beaker. When used, a stir bar is placed in the beaker, for example for rotating using a magnetic stir plate located beneath the spectrophotometer. Alternatively, direct mechanical stirring may be used. A stream of $CO_2$ gas may be delivered into the physiological media in the infinite sink to maintain its pH, e.g. at physiological pH (7.3-7.4), for the duration of the study. A thermocouple placed in the infinite sink physiological fluid may be used to ensure that a baseline verification of maintaining a constant temperature of 30 to 37° C. is performed.

Once the apparatus has been readied for use, the instruments to measure pH, Raman spectra, optical density, temperature, or other parameters are turned on. Conveniently, these data gathering instruments may be linked to and/or controlled by a computer to collect the instrument data and for verifying that they are working properly. The test formulation is introduced into the cassette chamber, for example through a catheter connected to the needle port or with a hypodermic needle through the septum and the collection of data is started. In general, experiments may be run for several hours to emulate the time course of uptake of protein and peptide drugs, or other therapeutic entities, from the administration site, e.g. a subcutaneous injection site. During this time sampling of the physiological buffer in the infinite sink is used to measure the amount of protein or peptide as well as specific formulation excipients that leave the cassette chamber to determine the concentration of these materials over the time course of the study.

The collected data is used to examine the physical properties of a protein or peptide drug and correlate changes in these properties with pH and concentration of formulation materials at the modelled injection site. The goal is to have a method that allows for rapid and accurate screening of formulation parameters that can improve the bioavailability of proteins and peptides delivered by SC injection.

Drug Formulations

The apparatus and methods of the present invention are generally applicable to modelling the behaviour of any drug, including small molecule drugs, and are particularly well suited to studying biotherapeutic drug formulations comprising antibodies, proteins or peptides. The techniques are applicable to any size or type of polypeptide from small peptides to polypeptides and proteins having molecular weights of up to or over 100 kDa. Accordingly, while for convenience, the methods herein are generally described by reference to "polypeptides", this should be taken to include shorter sequences of amino acids (e.g., from 2, 3, 4, 5 or 10 amino acids in length to 30, 40 or 50 amino acids in length), sometimes referred to in the art as peptides. The term should also be taken to include polypeptides having secondary, tertiary or quaternary structure generally referred to as proteins, as well as multidomain proteins.

Example of suitable classes of polypeptides that may be modified in accordance with the present invention include erythropoietins (EPO), interferons, interleukins, chemokines, lymphokines, cytokines, insulin, monoclonal antibodies and fragments, recombinant antibodies and fragments, blood-clotting factors, colony-stimulating factors (CSFs), growth hormones, plasminogen activators, virally-derived peptides, reproductive hormones and therapeutic enzymes. Specific examples of polypeptides that may be employed include colony stimulating factor (CSF), granulocyte colony stimulating factor (G-CSF), granulocyte macrophage colony stimulating factor (GM-CSF), Factor VIIa, Factor VIII, Factor IX, human growth hormone (hGH), DNase, insulin, glucagon, VEGF, VEGF receptor, TNF, TNF receptor, platelet-derived growth factor (PDGF), tissue plasminogen activator (tPA), erythropoietin (EPO), enfurvirtide, insulin-like growth factor (IGF), nerve growth factor (NGF), IL-1, IL-2, IL-6, IL-10, IL-12, IL-18, IL-24, interferon beta-1a, interferon beta-1b, interferon alpha-2a, interferon alpha-2b, interferon alpha, or interferon gamma.

In the present invention, references to polypeptides that are antibodies includes immunoglobulins whether natural or partly or wholly synthetically produced. The term also covers any polypeptide or protein comprising an antigen-binding domain. Antibody fragments, which comprise an antigen-binding domain include Fab, scFv, Fv, dAb, Fd fragments, diabodies, triabodies or nanobodies. It is possible to take monoclonal and other antibodies and use techniques of recombinant DNA technology to produce other antibodies or chimeric molecules, which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2,188,638 A or EP 0 239 400 A. Antibodies can be modified in a number of ways and the term should be construed as covering any specific binding member or substance having an antibody antigen-binding domain with the required specificity. Thus, this term covers antibody fragments and derivatives, including any polypeptide comprising an immunoglobulin-binding domain, whether natural or wholly or partially synthetic. Chimeric molecules comprising an immunoglobulin binding domain, or equivalent, fused to another polypeptide are therefore included. Cloning and expression of chimeric antibodies are described in EP 0 120 694 A and EP 0 125 023 A.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242; 423-426, 1988; Huston et al, PNAS USA, 85: 5879-5883, 1988); (viii) bispecific single chain Fv dimers (PCT/US92/09965) and (ix) "diabodies", multivalent or multispecific fragments constructed by gene fusion (WO 94/13804; Holliger et al, P.N.A.S. USA, 90: 6444-6448, 1993). Fv, scFv or diabody molecules may be stabilised by the incorporation of disulphide bridges linking the VH and VL domains (Reiter et al, Nature Biotech, 14: 1239-1245, 1996). Minibodies comprising a scFv joined to a CH3 domain may also be made (Hu et al, Cancer Res., 56: 3055-3061, 1996).

The protein or peptide formulations may, in addition to one or more active ingredients, also include other components for increasing its shelf life, its efficacy in the body and/or its solubility. These pharmaceutically acceptable vehicles are well known and will be adapted by the person skilled in the art and include, in addition to the protein or peptide drug, a pharmaceutically acceptable excipient, carrier, buffer, stabilizer or other materials well known to those skilled in the art. For formulations administered by subcutaneous injection these additional components may be included to control the pH, isotonicity and/or stability of the formulation and include isotonic vehicles, such as Sodium Chloride Injection, Ringer's Injection, Lactated Ringer's Injection, preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG). In the formulation, a typical protein or peptide dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 or IgG4 isotype. In the methods of the present invention, the identity and amount of such components can be varied and the effect of the variation then tested to determine its effect on the behaviour of the formulation, and in particular the therapeutic protein or peptide, upon administration. The present invention may be used to study the effects of different physical and chemical degradation pathways of polypeptide, peptide or antibody drug formulations, in order to find components or conditions optimised to minimise loss of the active ingredient in the formulation and/or during the process of administration.

Example 1

General Description

Figure 2:
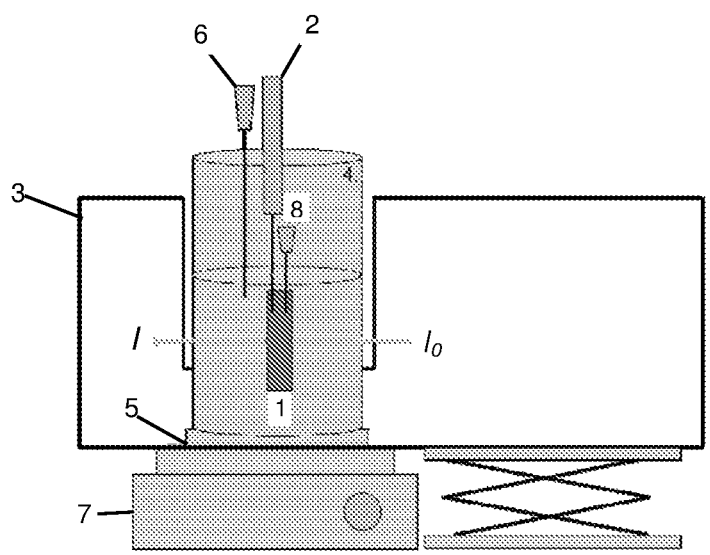
FIG. 2. The system depicted in FIG. 1 linked to a spectrophotometer and magnetic stirrer.

The system designed for monitoring the stability of biopharmaceuticals after subcutaneous (SC) injection is schematically presented in FIGS. 1 and 2. The system consists of a simulated subcutaneous injection site composed of a membrane cassette 1 with the membrane permeability modified to simulate the diffusional properties of the subcutaneous tissue and filled with components commonly found in the extracellular space of hypodermis, a pH probe 2 for monitoring the pH of the injection site, spectrophotometer 3 for monitoring the optical density of the material within the cassette, a large beaker 4 acting as the infinite sink of the body and containing salts and a buffer system similar to the ones found in interstitial fluid. In addition, the system contains a heating mechanism comprising a heat pad 5 and thermocouple 6 to maintain the temperature of the system at a physiological temperature between 30 and 37° C. and a magnetic stirrer 7 and a stir bar (not shown) to aid distributing the heat evenly and to mimic convection taking place in the subcutaneous tissue. Other instrumentation, such as but not limited to a Raman probe 8, can also be inserted into the injection site to monitor the conformational changes of the protein or peptides in detail after the injection. Unlike diffusion based systems, this allows measurements to be made in the interior of the chamber, as well as in the external sink.

Figure 3:
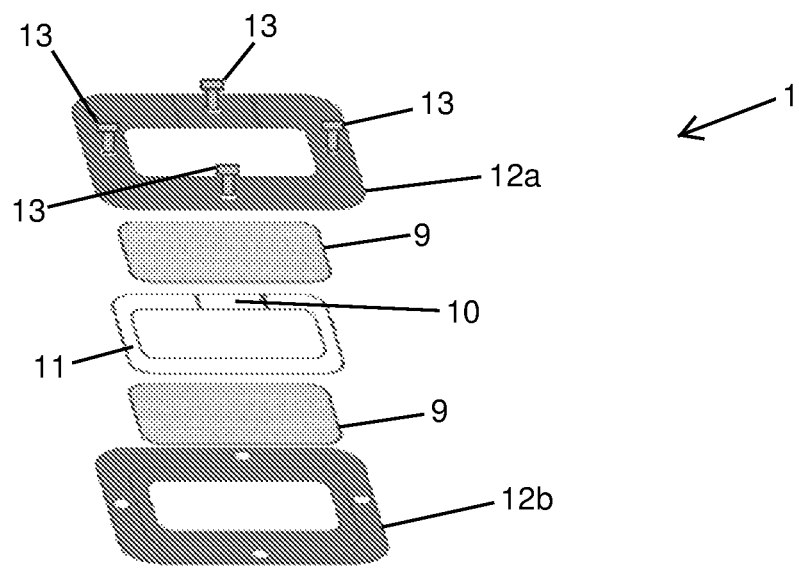
FIG. 3. Membrane cassette assembly with modified membranes and holes for pH probe and hypodermic needle through the plastic frame and the septum.

An example of the construction of the membrane cassette 1 is shown in FIG. 3. Two sheets of a modified dialysis membrane 9 are mounted in a membrane cassette 1 on either side of a septum 10 that acts as spacer and a port through which materials may be introduced into the membrane cassette, for example formed from silicone, separated by a spacer 11 to provide a chamber once the two halves of the cassette 12a and 12b are locked into place with locking pins 13. The septum 10 allows the contents of the membrane cassette to be monitored using one or more probes that may conveniently access the cassette through the membrane, e.g. where it is transparent to radiation, in a needle-type format through the septum, and/or via one or more ports provided in the membrane cassette.

Buffer Solution

The buffer solution used as the infinite sink in the system and for simulating conditions at an injection site was prepared by dissolving 6.4 g of NaCl, 0.09 g of $MgCl_2$ (hexahydrate), 0.4 g of KCl, 0.2 g of $CaCl_2$ (dihydrate) and 2.1 g of $Na_2HCO_3$ in 1 liter of deionised water as described in US 2003/0077655. All the reagents were purchased from Sigma Aldrich. Upon usage of the buffer, the pH of the solution was adjusted to and maintained at 7.35-7.4 by bubbling $CO_2$ gas through the buffer. The hydrostatic pressure within the simulated injection site can be adjusted by increasing the volume, and thus the height, of the buffer above the cassette.

Membrane

As an example, the membrane used in the system was Biodesing dialysis tubing with a molecular weight cut off diameter of 14000 Da. A 3 cm piece of the tubing was cut and the edges were removed to form two sheets of membrane. These sheets of membrane, whilst not separated from each other, were fully hydrated by soaking in deionised water and subsequently placed on Styrofoam covered with aluminium foil. The membrane permeability was then modified using a DERMAROLLER microneedle device. The membrane used can be transparent. The original permeability characteristics should probably not exceed the molecular weight of the protein/peptide of interest by approximately 30 times, for example for a methylene blue (MW.about.350 Da) two phase diffusion (first through the perforations and after a short lag time also rapidly through the membrane itself) was seen through the modified membrane with cut off of 14000 MWCO. In contrast, for rhodamine (MW.about.500 Da) the diffusion through the same membrane took place in one phase. The holes can be made with a DERMAROLLER microneedle device, or with any other method producing size and spatial distribution of holes suitable for the application. The diameter of the holes should be between 0.1 and a 10 micrometers and the spacing between any two adjacent holes between 0.1 and 10 mm.

Figure 4:
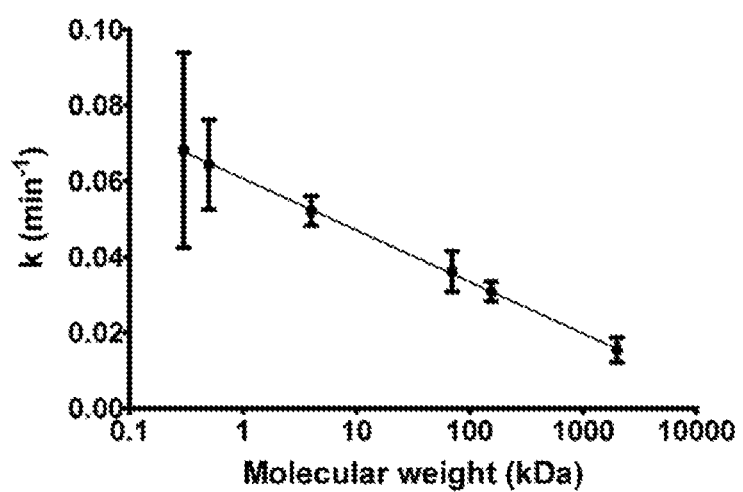
FIG. 4. The rate constant of diffusion (k) as a function of logarithm of the molecular weight of the sample ($r^2$=0.9996).
Figure 5:
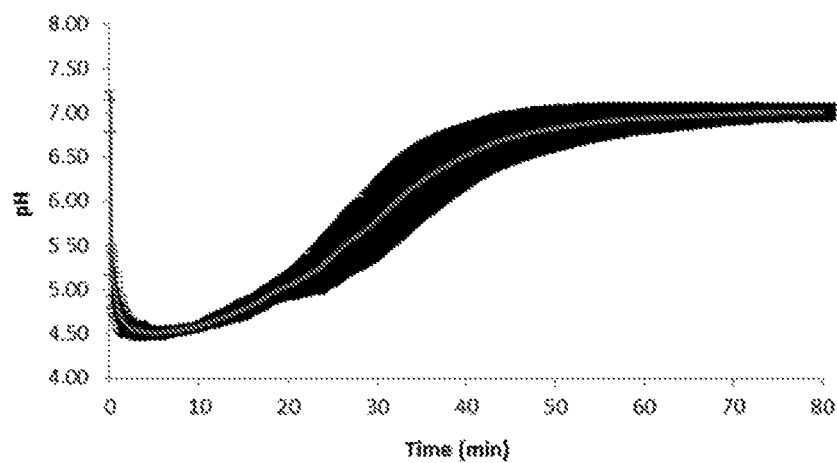
FIG. 5. Reproducibility of pH measurements as evaluated by injecting pH 4 calibration buffer into the simulated injection site and monitoring the pH change over time. The buffer used as the infinite sink was phosphate buffered saline (PBS) at pH 7.4.

As an example (FIG. 4), for a series of fluorescent small organic molecules (methylene blue and rhodamine) and fluorescently labelled dextrans with molecular weights between 4 kDa and 2 MDa, the rate constant of diffusion (k, $[min^{-1}]$) through the membranes after the modification followed the equation $k=-0.01362 \log_{10}$ (MW of the compound)$+0.06065$. ($R^2=0.9996$)

For holding the modified membranes, a Slide-a-lyzer dialysis cassette (Thermo Scientific) was disassembled and the original membranes of the cassette removed. For the purposes of re-assembling the cassette with the modified membranes, a screw hole of 15 mm diameter was drilled through the two plastic pieces in the middle of each of the sides of the cassette (see FIG. 3). The cassette also had a hole drilled for a needle pH probe (diameter 1.8 mm) and other holes for hypodermic needles for the purposes of, including but not limited to, injecting the sample and inserting a Raman probe and/or pressure transducer to the cassette. As shown in FIG. 3 the modified membranes were placed on each side of the septum. Optionally, a small magnetic stir bar (2 mm×2 mm×2 mm) can also be placed in between the membranes (within the cassette chamber). The pH probe was placed between the membranes through the septum and the hole drilled in the plastic frame. The system was then clamped with the screws.

The cassette was filled with an extracellular matrix component, such as but not limited to hyaluronic acid. Hyaluronic acid sodium salt from *Streptococcus equi*, purchased from Sigma-Aldrich, was dissolved in the buffer solution at a concentration of 5 mg/ml. The cassette filled with the extracellular matrix component was then placed in the infinite sink of the buffer and pH inside the cassette was monitored and allowed to reach equilibrium. Once equilibrium was achieved, sample was injected to the simulated injection site.

After the injection, the optical density and the pH at the injection site were monitored. In addition to these in situ measurements, aliquots of the buffer in the infinite sink can be taken and analysed to monitor the diffusion of the different components of the formulation.

Example 2: The Simulated Bioavailability of Levemir Formulation

Figure 6:
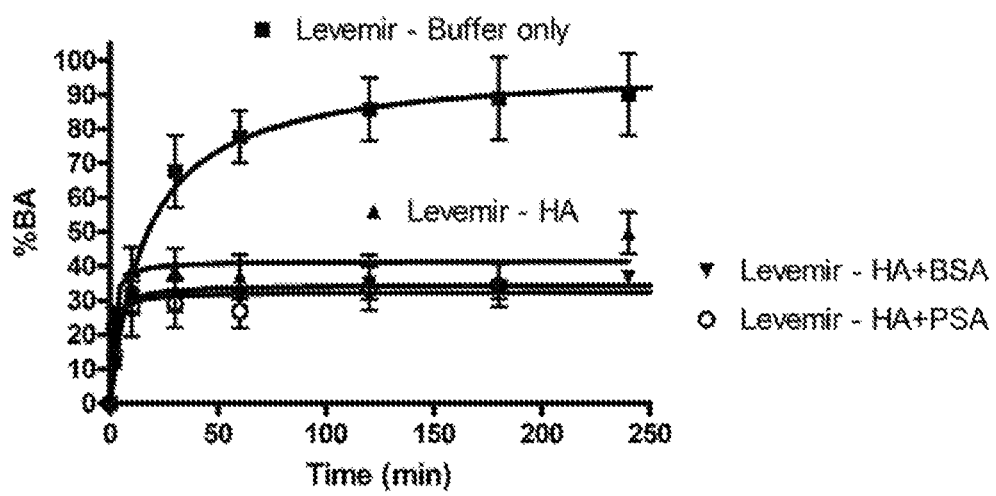
FIG. 6. The simulated bioavailability (% BA) profiles of Levemir as determined using the current invention with buffer only in the cassette, 5 mg/ml solution of hyaluronic acid (HA) in the cassette, hyaluronic acid and 10 mg/ml bovine serum albumin (HA+BSA) and hyaluronic acid and 10 mg/ml porcine serum albumin (HA+PSA) in the cassette. The data represents mean±standard deviation, n=3.
Figure 8:
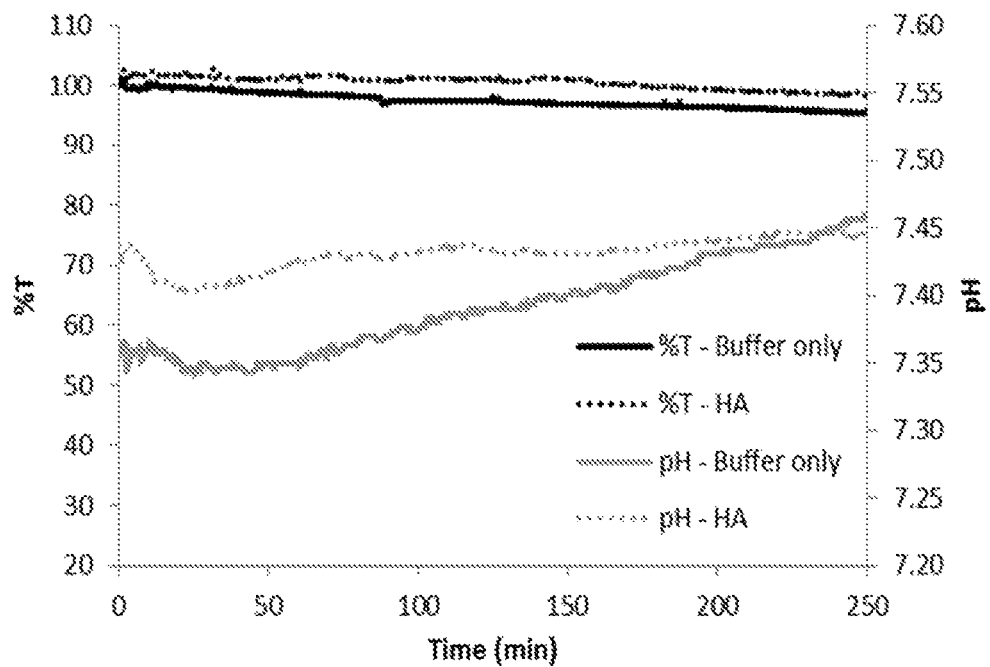
FIG. 8. In situ time profiles for protein solubility (% T, black lines) and pH in the membrane cassette after an injection of Levemir formulation as measured with the system described in the current patent with buffer only in the cassette (solid lines) and with 5 mg/ml hyaluronic acid (HA) in the cassette (dotted lines).

Levemir (Novo Nordisk) is a trade name for insulin detemir that is an insulin analogue with a myristic acid side chain attached to the peptide backbone. The molecule is known to be 98% bound to albumin via the side chain in blood plasma. The simulated bioavailability of the Levemir formulation was tested using the current invention by injecting 0.5 ml of the formulation into the cassette, taking samples from the buffer bath at different time points and determining the detemir content in the aliquots as per U.S. Pat. No. 6,620,780 (U.S. Ser. No. 09/861,687) using high performance liquid chromatography (HPLC). The results of the experiment are shown in FIG. 6. When the formulation was injected into a cassette containing only the physiological buffer of the buffer bath, the formulation was found to be 100% bioavailable. With the addition of hyaluronic acid (HA, sodium salt from *streptococcus equii*, Sigma Aldrich) solution (5 mg/ml) into the cassette, the simulated bioavailability of the formulation decreased to approximately 40%. With the addition of bovine serum albumin (Sigma Aldrich) and porcine serum albumin (Sigma Aldrich) into the HA solution at 10 mg/ml the simulated bioavailability of the Levemir formulation decreased slightly further. FIG. 8 shows results of in situ measurement of protein solubility as measured by % T and pH change within the cassette over the course of the experiment with buffer only in the cassette and for experiment with added HA in cassette. Each plot represents mean from three repeated measurements. The data demonstrate that despite the large differences in the simulated bioavailability for the formulation with buffer only in the cassette compared to HA in the cassette (100% vs. ~40%), the formulation does not exhibit instability in the form of precipitation within the injection site.

Example 3: In Situ Measurement of Protein Stability and pH Time Profiles of a Generic Insulin Formulation After its Injection into the Cassette A generic 500 IU/ml insulin formulation was prepared by dissolving 18.2 mg/ml of human recombinant insulin (Sigma Aldrich), 2.5 mg/ml of m-cresol (Sigma Aldrich), 16 mg/ml of glycerol and 0.085 mg/ml of zinc oxide (Sigma Aldrich)) in 0.05 M sodium acetate (Sigma Aldrich) buffer and HCl and NaOH were used for adjusting the formulation pH to 3.5.

0.5 ml of the generic insulin formulation was injected into the cassette of the current invention filled with physiological buffer solution and the pH and protein solubility, in this case determined by % T at 350 nm, were monitored in situ. These data show that upon injection (Time=0 min) the pH within the cassette decreased to a value close to the formulation pH value (~3.5). Shortly after injection, the protein solubility level decreased as indicated by the drop in % T. As the environment within the cassette equilibrated with the surrounding physiological conditions and the pH shifted towards 7.4, the protein re-solubilised as indicated by the increase in the % T level. The release profile of an excipient, m-cresol, from the injection site was determined from aliquots taken from the surrounding buffer bath at different time points by HPLC following the method specified in "Biodegradation characterisation and kinetics of m-cresol by Lysinibacillus cresolivorans" in Water SA (Online) vol.

Figure 7:
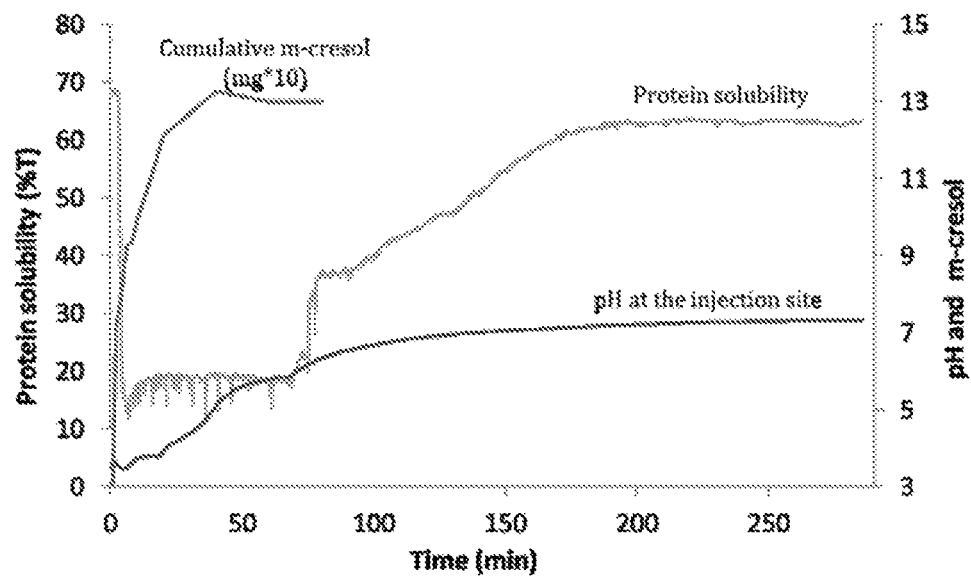
FIG. 7. In situ protein solubility (% T) and pH time profiles for a generic insulin formulation injected into the cassette, and the cumulative amount of an excipient, m-cresol, released from the injection site over time determined from aliquots taken from the bath. For clarity of presentation, the scale for the cumulative amount of m-cresol is multiplied by 10.

37 no. 1 Pretoria January 2011. These data shown in FIG. 7 demonstrate that all the excipient contained within the injected formulation has left the injection site in less than 50 minutes.

All documents mentioned in this specification are incorporated herein by reference in their entirety.

The invention claimed is:

1. An in vitro method of determining a change in a property of a drug formulation that occurs on administration, the method employing an apparatus that comprises:
   a membrane cassette comprising a chamber having a membrane, the membrane having perforations through which components of the drug formulation are capable of diffusing for simulating changes that occur on administration of the drug formulation, wherein the chamber of the membrane cassette contains one or more components found in the site of administration for simulating conditions at the site;
   a bath that contains a liquid medium and said membrane cassette submerged therein;
   a probe capable of detecting a change in a property of the drug formulation inside the membrane cassette, and optionally a change in a property of the drug formulation in the bath,
   wherein the method comprises the steps of:
   (a) arranging the membrane cassette in the bath;
   (b) introducing the drug formulation into the chamber of the membrane cassette by injection;
   (c) optionally changing one or more components or conditions of the drug formulation or the liquid medium; and
   (d) determining the change of the property of the drug formulation using the probe.

2. An apparatus for determining a change in a property of a drug formulation that occurs on administration, the apparatus comprising:
   a membrane cassette comprising a chamber having a membrane, the membrane cassette having an injection port for introducing samples of drug formulation or probes into the chamber of the membrane cassette, the membrane cassette allowing components of the drug formulation to diffuse for simulating changes that occur on administration of the drug formulation, wherein the chamber of the membrane cassette contains one or more components found in the site of administration for simulating conditions at the site;
   a liquid medium;
   a bath that contains the liquid medium and the membrane cassette submerged therein;
   a probe capable of detecting a change in a property of the drug formulation inside the membrane cassette, [and optionally a change in a poperty of the drug formulation in the bath,]
   wherein in use the membrane cassette is arranged in the bath and the drug formulation is introduced by injection into the chamber of the membrane cassette thereby enabling changes in the property of the drug formulation to be determined using the probe.

3. The apparatus of claim 2, wherein the membrane cassette is adapted for modelling administration of a drug formulation to the eye, wherein the chamber of the membrane cassette contains one or more hydrogels for modelling the vitreous humour of the eye and a membrane for modelling the sclera and the retina [optionally wherein the hydrogels comprise collagen and hyaluronic acid].

4. The apparatus of claim 2, wherein the membrane cassette is adapted for modelling administration via an intramuscular route, wherein the chamber of the membrane cassette contains one or more materials selected from actin, myosin, glycogen, myoglobin, collagen, troponin and/or tropomysin and a membrane having permeability properties that simulate muscle.

5. The apparatus of claim 2, wherein the membrane cassette is adapted for modelling administration via a subcutaneous injection route, wherein the chamber of the membrane cassette contains hyaluronic acid and collagen.

6. The apparatus of claim 2, wherein the membrane cassette is adapted for modelling administration via an intradermal injection route, wherein the chamber of the membrane cassette contains collagen and dermatan sulphate.

7. The apparatus of claim 2, wherein the membrane cassette is adapted for modelling administration via an intrathecal route, wherein the chamber of the membrane cassette contains simulated cerebrospinal fluid as a buffer solution.

8. The apparatus of claim 2, wherein the membrane cassette is adapted for modelling administration via an epidural route, wherein the chamber of the membrane cassette contains one or more of collagen and hyaluronic acid for modelling filling the epidural space.

9. The apparatus of claim 2, wherein the drug formulation is a polypeptide, peptide or antibody formulation.

10. The apparatus of claim 2, wherein the chamber of the membrane cassette contains components found in the extracellular matrix for simulating conditions at an injection site.

11. The apparatus of claim 10, wherein the extracellular matrix component comprises a hyaluronic acid or a salt thereof, a collagen, a fibronectin, a laminin, dermatan sulphate and/or one or more cell lines.

12. The apparatus of claim 2, wherein the chamber of the membrane cassette has a volume between 0.5 ml and 10 ml.

13. The apparatus of claim 2, wherein the membrane is transparent.

14. The apparatus of claim 2, wherein the membrane is an unmodified microfiltration membrane or dialysis membrane.

15. The apparatus of claim 2, wherein the membrane is formed from regenerated cellulose, cellulose acetate or ester or mixture of thereof, polycarbonate, polyester, polyestersulfone, nylon, polyvinyldinefluoride (PVDF), polyvinylchloride (PVC) or polytetrafluoroethylene (PTFE).

16. The apparatus of claim 2, wherein the membrane [injection port] comprises perforations [in the membrane are obtainable by treatment with a microneedle roller or a laser].

17. The apparatus of claim 16, wherein the perforations are between about 0.1 and about 200 microns in size.

18. The apparatus of claim 16, wherein the perforations are between about 1 micron and 10 mm apart.

19. The apparatus of claim 2, wherein the apparatus comprises a heat control and measurement system.

20. The apparatus of claim 2, wherein the bath has a stirrer.

21. The apparatus of claim 2, wherein the apparatus comprises a temperature measurement system and control for maintaining temperature control and maintaining convective flow to simulate a subcutaneous injection site.

22. The apparatus of claim 2, wherein the liquid medium is a buffer solution.

23. The apparatus of claim 2, wherein the apparatus comprises a plurality of probes.

24. The apparatus of claim 23, wherein the drug formulation comprises a protein drug and the probes comprise a Raman probe and/or fluorescence spectroscopy probe for monitoring the conformational changes the protein drug undergoes after injection and for monitoring said protein drug concentrations in the liquid medium inside the chamber [at least one of the buffer solution and the chamber].

25. The apparatus of claim 23, wherein the probes comprise a temperature probe, a pressure transducer, a pH probe, or a probe for measuring optical density for determining precipitation of components of the formulation.

26. The apparatus of claim 25, wherein said probe for measuring optical density for determining precipitation of components of the formulation is a spectrophotometer.

27. The apparatus of claim 2, wherein the injection port is a port septum.

* * * * *